(12) United States Patent
Bogdanowicz

(10) Patent No.: US 7,321,795 B2
(45) Date of Patent: Jan. 22, 2008

(54) COMPOSITIONS FOR ELECTRIC STIMULATION OF THE EYE

(76) Inventor: Les Bogdanowicz, 1307 W. Filmore, Chicago, IL (US) 60607

( * ) Notice: Subject to any disclaimer, the term of this patent is extended or adjusted under 35 U.S.C. 154(b) by 73 days.

(21) Appl. No.: 10/808,915

(22) Filed: Mar. 24, 2004

(65) Prior Publication Data
US 2005/0010266 A1    Jan. 13, 2005

Related U.S. Application Data

(60) Provisional application No. 60/457,389, filed on Mar. 24, 2003.

(51) Int. Cl.
*A61N 1/18* (2006.01)

(52) U.S. Cl. ............... 607/53; 607/54; 351/49; 351/160 R

(58) Field of Classification Search ......... 607/53–54, 607/139, 141; 623/6.11, 6.22, 6.63; 351/49, 351/160 R
See application file for complete search history.

(56) References Cited

U.S. PATENT DOCUMENTS

| | | | |
|---|---|---|---|
| 2,760,483 A | 8/1956 | Tassicker | |
| 4,272,910 A | 6/1981 | Danz | |
| 5,016,633 A | 5/1991 | Chow | |
| 5,024,223 A | 6/1991 | Chow | |
| 5,109,844 A * | 5/1992 | de Juan et al. | 607/53 |
| 5,522,864 A | 6/1996 | Wallace et al. | |
| 5,556,423 A | 9/1996 | Chow et al. | |
| 5,868,728 A | 2/1999 | Giungo et al. | |
| 5,895,415 A | 4/1999 | Chow et al. | |
| 5,935,156 A | 8/1999 | Chandler et al. | |
| 6,035,236 A | 3/2000 | Jarding et al. | |
| 6,123,668 A * | 9/2000 | Abreu | 600/405 |
| 6,230,057 B1 | 5/2001 | Chow et al. | |
| 6,331,523 B1 | 12/2001 | Kljavin et al. | |
| 6,427,087 B1 * | 7/2002 | Chow et al. | 607/54 |
| 6,792,314 B2 * | 9/2004 | Byers et al. | 607/53 |
| 6,804,560 B2 | 10/2004 | Nisch et al. | |
| 6,847,847 B2 | 1/2005 | Nisch et al. | |
| 2002/0055724 A1 | 5/2002 | Hughes | |
| 2002/0087202 A1 * | 7/2002 | Chow et al. | 607/53 |
| 2003/0014089 A1 * | 1/2003 | Chow et al. | 607/54 |
| 2003/0080314 A1 | 5/2003 | Nisch et al. | |
| 2003/0139784 A1 * | 7/2003 | Morimoto et al. | 607/54 |

(Continued)

FOREIGN PATENT DOCUMENTS

EP    0 940 118 A3    3/1999

OTHER PUBLICATIONS

Armington, John C., Effects of Stimulus Location and Pattern Upon the Visually Evoked Cortical Potential and the Electroretinogram, Intern. J. Neuroscience, 1981, vol. 14, pp. 169-178.

(Continued)

*Primary Examiner*—Carl Layno
*Assistant Examiner*—Deborah Malamud
(74) *Attorney, Agent, or Firm*—Bell, Boyd & Lloyd LLP

(57) ABSTRACT

The present application discloses an ocular stimulation device including a contact lens with a member embedded in a surface thereof for electrically stimulating an eye of a wearer of the lens.

19 Claims, 17 Drawing Sheets

U.S. PATENT DOCUMENTS

| | | | |
|---|---|---|---|
| 2003/0153067 A1 | 8/2003 | Stett et al. | |
| 2003/0158588 A1* | 8/2003 | Rizzo et al. | 607/54 |
| 2004/0078064 A1* | 4/2004 | Suzuki | 607/54 |
| 2004/0117011 A1* | 6/2004 | Aharoni et al. | 623/6.11 |

OTHER PUBLICATIONS

Baylor, et al., Electrical Respones of Single Cones in the Retina of the Turtle, J. Physiol. (1970), 207, pp. 77-92.
Baylor, et al., Transmission from Photoreceptors to Ganglion Cells in Turtle Retina, J. Physiol. (1977), 271, pp. 391-424.
Belgum et al., Synaptic Transfer of Rod Signals to Horizontal and Bipolar Cells in the Retina of the Toad (*Bufo Marinus*), Journal of Physiology (1988), 396, pp. 225-245.
Bloomfields, et al., Roles of Aspartate and Glutamate in Synaptic Transmission in Rabbit Retina, The American Physiological Society, 1985.
Bortoff et al., An Electrical Model of the Vertebrate Photoreceptor Cell, Vision Res. vol. 7, pp. 253-263, Pergamon Press 1967.
Bortoff et al., Simultaneous Recording of Photoreceptor Potentials and the PIII Component of the ERG[1], Vision Res., vol. 5, pp. 527-533. Pergamon Press 1965.
Carpenter, H.S., Electrical Stimulation of the Human Eye in Different Adaptational States, J. Physiol. (1972), 221, pp. 137-148.
Charles, Steve, Electrical Signals of the Retinal Microcircuitry, Reprinted from Records re: Physiology of the Human Eye and Visual System. Hagerstown, Harper and Row, 1979.
Copenhagen, et al., Kinetics of Synaptic Transmission from Photoreceptors to Horizontal and Bipolar Celles in Turtle Retina, Vision Res. 23, 363-369 1983.
Dawson et al., The electrical stimulation of the retina by indwelling electrodes, Invest. Ophthalmol. Visual Sci., Mar. 1977.
Dowling et al., Visual Adaptation in the Retina of the Skate, The Journal of General Physiology, vol. 56, 1970.
Eagle, et al., Retinal Pigment Epithelial Abnormalities in Fundus Flavimaculatus, Ophthalmology, Dec. 1980, vol. 87, No. 12.
Erickson, et al., Retinal Detachment in the Cat: The Outer Nuclear and Outer Plexiform Layers, Investigaive Ophthalmology & Visual Science, Jul. 1983.
Fenwick et al., Changes in the Pattern Reversal Visual Evoked Potential as a Function of Inspired Nitrous Oxide Concentration, Elsevier Scientific Publishers of Ireland, Ltd., Aug. 24, 1983, pp. 178-183.
Gernandt et al., Single Fibre Analysis of Inhibition and the Polarity of the Retinal Elements, The Nobel Institute for Neurophysiology, Karolinska Institute, Stockholm, Sweden, Apr. 23, 1947, pp. 295-301.
Green et al., Retinal Mechanisms of Visual Adaptation in the Skate, The Journal of General Physiology, vol. 65, 1975, pp. 483-502.
Humayun, Mark S., Intraocular Retinal Prosthesis, Tr. Am. Ophth. Soc., vol. 99, 2001, pp. 271-300.
Kaneko, Akimichi, Physiological and Morphological Identification of Horizontal, Bipolar and Amacrine Cells in Goldfish Retina, J. Physiol. (1970), 207, pp. 623-633.
Kaneko et al., Recording Site of the Single Cone Response Determined by an Electrode Marking Technique[1], Vision Res., vol. 7, pp. 847-851. Pergamon Press 1967.
Kolb, Helga, The Architecture of Functional Neural Circuits in the Vertebrate Retina, Investigative Ophthalmology & Visual Science, Apr. 1994, vol. 35, No. 5, pp. 2385-2404.
Massey et al., The Effects of 2-Amino-4-Phosphonobutyric Acid (APB) on the ERG and Ganglion Cell Discharge of Rabbit Retina, Vision Res. vol. 23, No. 12, pp. 1607-1613, 1983.
Neher, et al., Single-channel currents recorded from membrane of denervated frog muscle fibres, Nature, vol. 260, Apr. 29, 1976, pp. 799-802.
Normann et al.l, A neural interface for a cortical vision prosthesis, Vision Research, 39, (1999), pp. 2577-2587.
Peyman et al., Subretinal Semiconductor Microphotodiode Array, Experimental Science, Ophthalmic Surgery and Lasers, Mar. 1998, vol. 29, No. 3, pp. 234-241.
Rauschecker et al., Sending Sound to the Brain, Science, vol. 295, Feb. 8, 2002, pp. 1025-1029.
Rovamo, et al., An Estimation and Application of the Human Cortical Magnification Factor, Exp. Brain Res. 37, 495-510 (1979).
Schwab, Martin E., Repairing the Injured Spinal Cord, Science, Fol. 295, Feb. 8, 2002, pp. 1029-1031.
Scribner et al., Intraocular Retinal Prosthesis Test Device, 23rd Annual International Conference of the IEEE Engineering in Medicine and Biology Society, Istanbul, Turkey, Oct. 2001.
Shannon, Robert V., A Model of Safe Levels for Electrical Stimulation, IEEE Transactions on Biomedical Engineering, vol. 39, No. 4, Apr. 1992, pp. 424-426.
Terr, et al., Histopathologic Study of the Cochlear Nuclei after 10 Years of Electrical Stimulation of the Humal Cochlea, The American Journal of Otology, vol. 9, No. 1, Jan. 1988, pp. 1-6.
Werblin, Frank, Synaptic Connections, Receptive Fields, and Patterns of Activity in the Tiger Salamander Retina, Investigative Ophthalmology & Visual Sicence, vol. 32, No. 3, Mar. 1991, pp. 459-482.
Werblin et al., Organization of the Retina of the Mudpupy, *Necturus maculosus*. II. Intracellular Recording, The Wilmer Institut, The Johns Hopkins University School of Medicine, Oct. 15, 1968, pp. 339-355.
New technique induces growth across spinal cord injury abstract, printed from http://www.mgh.harvard.edu/depts/pubaffairs/Releases/May99_spinal_cord.htm, printed on Jul. 6, 2001.
An Overview of Spinal Cord Research abstract, printed from http://www.spinal-research.org/res.htm, printed on Jul. 6, 2001.
An electrophysiological investigation of the functional regeneration promoted by grafts of olfactory bulb ensheathing cells in the adult mammalian spinal cord abstract, printed from http://www.spinal-research.org/riddell-barnett.html, printed on Jul. 6, 2001.
Microstimulation of the Lumbosacral Spinal Cord abstract, printed from http://feswww.fes.cwru.edu/projects/wmgnih1.htm, printed on Jul. 6, 2001.
Medicare's Coverage Policies on Electrical Stimulation for Fracture Healing abstract, printed from http://www.hcfa.gov/coverage/8b3.j2.htm, printed on Jul. 6, 2001.
Applied Electric Fields in the Treatment of Bone Fractures abstract, printed from http://www.wpi.edu/~grovers/PH3301/emtherapy/SallyHouse/SallyHouse.html, printed on Jul. 6, 2001.
Electrical stimulation of hard and soft tissues in animal models abstract, printed from http://gateway.nlm.nih.gov/gw/Cmd?GMResults, printed on Aug. 20, 2001.
A constant cathodic potential device for faradic stimulation of osteogenesis abstract, printed from http://www.ncbi.nlm.nih.gov/entrez/query.fcgi?cmd=Retrieve&db=PubMed&list_uids=7670693&dopt=Abstract, printed on Aug. 27, 2001.
Medullary osteogenesis with platinum cathodes abstract, printed from http://gateway.nlm.nih.gov/gw/Cmd?GMResults, printed on Aug. 20, 2001.
Electrical stimulation with bone and wound healing abstract, printed from http://www.ncbi.nlm.nih.gov/entrez/query.fcgi?cmd=Retrieve&db=PubMed&list_uids=11344981&dopt=Abstract, printed on Aug. 27, 2001.
Continuously infused calcium hydroxide: its influence on hard tissue repair abstract, printed from http://www.ncbi.nlm.nih.gov/entrez/query.fcgi?CMD=Display&DB=PubMed, printed on Aug. 20, 2001.
Direct current electrical bone growth stimulation for spinal fusion abstract, printed from http://gateway.nlm.nih.gov/gw/Cmd?GMResults, printed on Aug. 20, 2001.
Electrical stimulation of bone growth with direct current abstract, printed from http://gateway.nlm.nih.gov/gw/Cmd?GMResults, printed on Aug. 20, 2001.
Electrical stimulation induces the level of TGF-Beta1 mRNA in osteoblastic cells by a mechanism involving calcium/calmodulin pathway abstract, printed from http://www.ncbi.nlm.nih.gov/entrez/query.fcgi?cmd=Retrieve&db=PubMed&list_uids=9268690&dopt=Abstract, printed on Aug. 27, 2001.
Electrode-oxygen consumption and its effects on tissue-oxygen tension. A study of mass spectrometry abstract, printed from http:// www.ncbi.nlm.nih.gov/entrez/query.fcgi?CMD=Display&DB=PubMed, printed on Aug. 20, 2001.

Cathodic oxygen consumption and electrically induced osteogenesis abstract, printed from http://www.ncbi.nlm.nih.gov/entrez/query.fcgi?CMD=Display&DB=PubMed, printed on Aug. 20, 2001.

Does Electrical stimulation of deaf cochleae prevent spiral ganglion degeneration? Abstract, printed from http://www.ncbi.nlm.nih.gov/entrez/query.fcgi?CMD=Display&DB=PubMed, printed Aug. 20, 2001.

Osteogenesis of electrically stimulated bone cells mediated in part by calcium ions abstract, printed from http://www.ncbi.nlm.nih.gov/entrez/query.fcgi?CMD=Display&DB=PubMed, printed on Aug. 20, 2001.

Chronic intracochlear electrical stimulation induces selective survival of spiral ganglion neurons in neonatally deafened cats abstract, printed from http://www.ncbi.nlm.nih.gov/entrez/query.fcgi?CMD=Display&DB=PubMed, printed on Aug. 20, 2001.

Chronic electrical stimulation by a cochlear implant promotes survival of spiral ganglion neurons after neonatal deafness abstract, printed from http://www.ncbi.nlm.nih.gov/entrez/query.fcgi?cmd=Retrieve&db=PubMed&list_uids=10464355&dopt=Abstract, printed on Aug. 27, 2001.

Cochlear pathology following chronic electrical stimulation using non charge balanced stimuli abstract, printed from http://www.ncbi.nlm.nih.gov/entrez/query.fcgi?cmd=Retrieve&db=PubMed&list_uids=10464355&dopt=Abstract, printed on Aug. 27, 2001.

Cochlear implant effects on the spiral ganglion abstract, printed from http://www.ncbi.nlm.nih.gov/entrez/query.fcgi?CMD=Display&DB=PubMed, printed on Aug. 20, 2001.

* cited by examiner

COMPOSITIONS FOR ELECTRIC STIMULATION OF THE EYE

CROSS-REFERENCE TO RELATED APPLICATIONS

This application claims priority from provisional patent application Ser. No. 60/457,389 filed on Mar. 24, 2003, which is incorporated herein by reference and made a part hereof.

FEDERALLY SPONSORED RESEARCH OR DEVELOPMENT

Not Applicable.

BACKGROUND OF THE INVENTION

Blindness can occur when any part of the vision system (the optics, the retina, the optic nerve or the visual cortex) are interrupted or destroyed. The leading cause of blindness in the developed world is Retinal Degeneration (RD). The two principle diseases resulting in RD are Age Related Macular Degeneration (AMD) and Retinitis Pigmentosa (RP). AMD is the leading cause of blindness in the developed world. According to a March 1997 review in the Optometry Journal, 10 percent of the U.S. population over the age of 52 has AMD and 33 percent of individuals over the age of 75 have AMD.

AMD can be categorized into two forms, a non-neovascular (dry, atrophic) form and a neovascular (wet, exudative) form. The non-neovascular form involves alterations of pigment distribution, loss of retinal pigment epithelium (RPE) cells and photoreceptors, and diminished retinal function due to an overall atrophy of the cells. The neovascular form of AMD involves proliferation of abnormal choroidal vessels, which penetrate the Bruch's membrane and RPE layer into the subretinal space forming extensive clots and scars. The cause of AMD is unknown.

RP is a name given to a large group of degenerative diseases. The dominant form of RP is associated with mutations in the visual pigment, rhodopsin protein. These mutations account for about 25 percent of RP cases in the U.S.

Normal retinal cell function is a photo-induced electrochemical reaction converting light energy into an electrical impulse. The photochemical reaction begins with the absorption of light by Rhodopsin. Rhodopsin breaks down into several intermediate compounds, but eventually forms metarhodopsin II (activated rhodopsin). This chemical causes electrical impulses that are transmitted via synapses to the first complex array of interneurons (bipolar cells and horizontal cells). These in turn connect to the ganglion cells, whose axons form the optic nerve.

The same electrical impulse travels to the visual cortex of the brain via the optic nerve and results in a vision sensation. With AMD, RP and other Retinal Degenerative (RD) diseases, photoreceptor retinal cells atrophy and eventually lose cell function. Since the bipolar and horizontal cells no longer receive neuronal signals, the retinal interneuronal layers undergo remodeling or arborization. The neural network is "pruned" and refined by mechanisms that include cell death, selective growth, loss of neurites and elimination of synapses (Neely and Nicholls, 1995). This natural phenomenon is related to the adage: "use it or lose it."

It has been demonstrated that electrical stimulation of ganglion cells shows a rescue or neurotrophic effect, which promotes cell survival. Specifically, several studies performed on spiral ganglion cells show a survival due to electrical stimulation from cochlear implants (Leake et al., 1991; Leake et al., 1999). Recently documented studies of implanted human subjects with Microphotodiode Arrays (MPDA) have shown an overall improvement in vision. The results indicate that the MPDA in effect has not restored vision in the specific area in which the implant is placed; instead, results indicate a neurotrophic rescue effect due to the electrical stimulation on the remaining retinal cells.

The application of electrical stimulation to organ systems other than the ocular system is known to promote and maintain certain cellular functions. Electrical stimulation has been documented in bone growth and spinal cord growth, as well as in cochlear cell survival as mentioned earlier (Dooley et al., 1978; Evans et al., 2001; Kane, 1988; Koyama et al., 1997; Lagey et al., 1986; Politis and Zanakis, 1988a; Politis and Zanakis, 1988b; Politis and Zanakis, 1989; Politis et al., 1988a; Politis et al., 1988b). Electrical stimulation has also been applied in Deep Brain Stimulators for Parkinson's Disease and Essential Tremor. This electrical stimulation temporarily disables the overactive cells that cause Parkinson's disease symptoms (O'Suilleabhain P. E., 2003).

Electrical stimulation of the ocular system has been under study for several decades. As early as the 1890's, scientists have been experimenting with the use of an electric current to produce an artificial vision sensation or phosphene. Brindley's work in the 1950's documents the thresholds needed to induce such a phosphene (Brindley 1955). There are also numerous amounts of animal work that suggest that the retina responds to externally applied electrical stimulation (Kuras, A. V., Khusainovene N P. 1981, Knighton, R. W. 1975, Humayun, M. S. 2001, Grumet, A. E. et. al. 2001).

Tassicker described the notion of an implanted artificial vision device in a U.S. patent in 1956 (U.S. Pat. No. 2,760,483). A light-sensitive selenium cell was placed behind the retina of a blind patient and transiently restored the patient's ability to perceive a sensation of light. Since then, several groups have been working to develop a device that can be implanted in place of the degrading photoreceptors. These groups attempt to restore vision by using photonic properties of semiconductors designed to mimic the electric charge that damaged retinal cells would otherwise generate. However, there are few devices or treatments available that can slow, stop or reverse retinal degeneration.

Recent studies of the electrical stimulation of the cut optic nerve show a survival of axotomized retinal ganglion cells in vivo. The conclusion from this experimentation demonstrates that electrical stimulation of the optical nerve enhances the survival of axotomized retinal ganglion cells in vivo due to electrical activation of their soma (Morimoto T., 2002).

These findings led me to find a means for providing electrical stimulation to a diseased eye in a minimally invasive manner, to stimulate the regrowth, rescue and survival of ocular neural tissue and the entire ocular system for the treatment of blinding diseases such as Retinitis Pigmentosa, Age Related Macular Degeneration, and other Retinal Degenerative diseases.

SUMMARY OF THE INVENTION

It is an advantage of the present invention to provide novel methods and apparatus for treating various diseases including Retinitis Pigmentosa and Age Related Macular Degeneration. Further, the present invention provides a device including a contact lens with a member embedded in a surface thereof for electrically stimulating an eye of a wearer of the lens.

These and other aspects and attributes of the present invention will be discussed with reference to the following drawings and accompanying specification.

DETAILED DESCRIPTION OF THE INVENTION

Figure 1:
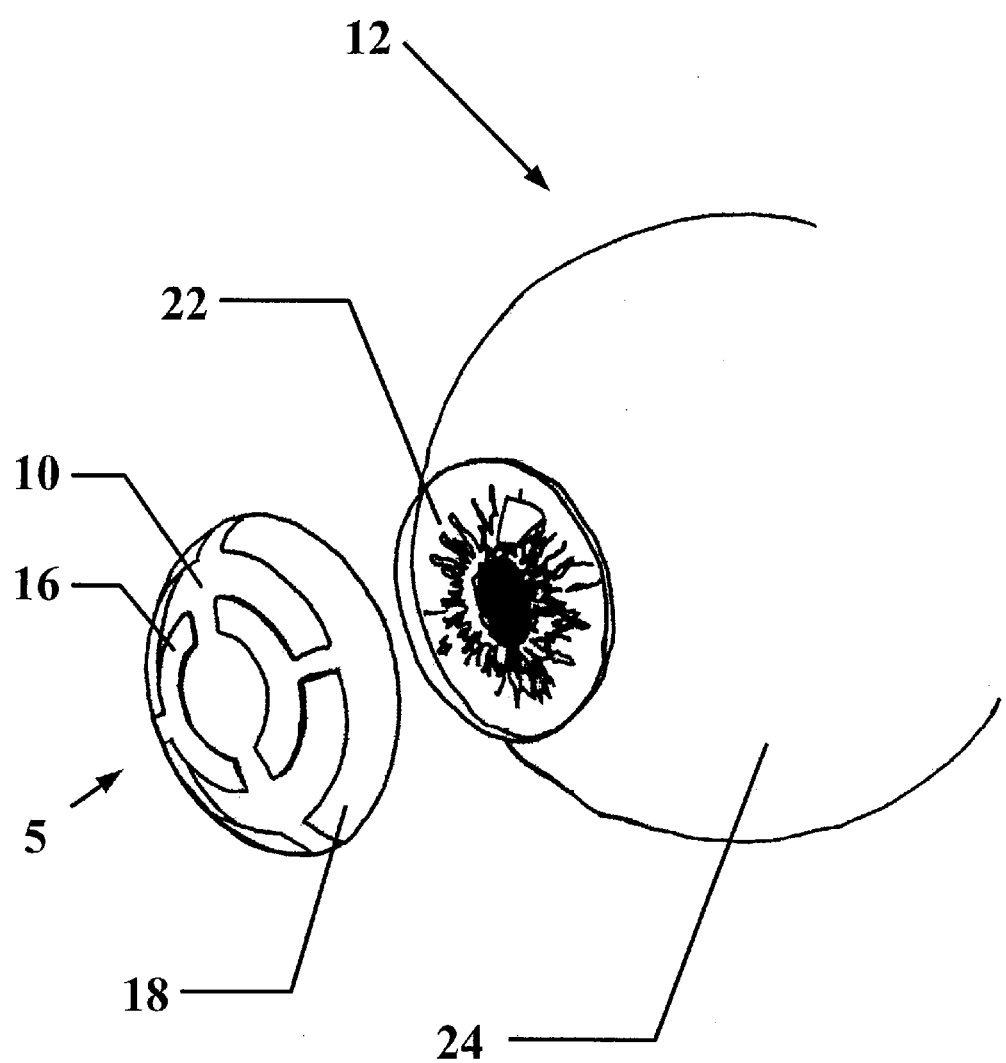
FIG. 1 is a diagram of the Ocular Stimulation Device (OSD) and the eye of a wearer of the device.

While this invention is susceptible of embodiment in many different forms, there is shown in the drawing, and will be described herein in detail, specific embodiments thereof with the understanding that the present disclosure is to be considered as an exemplification of the principles of the invention and is not intended to limit the invention to the specific embodiments illustrated.

Figure 4:
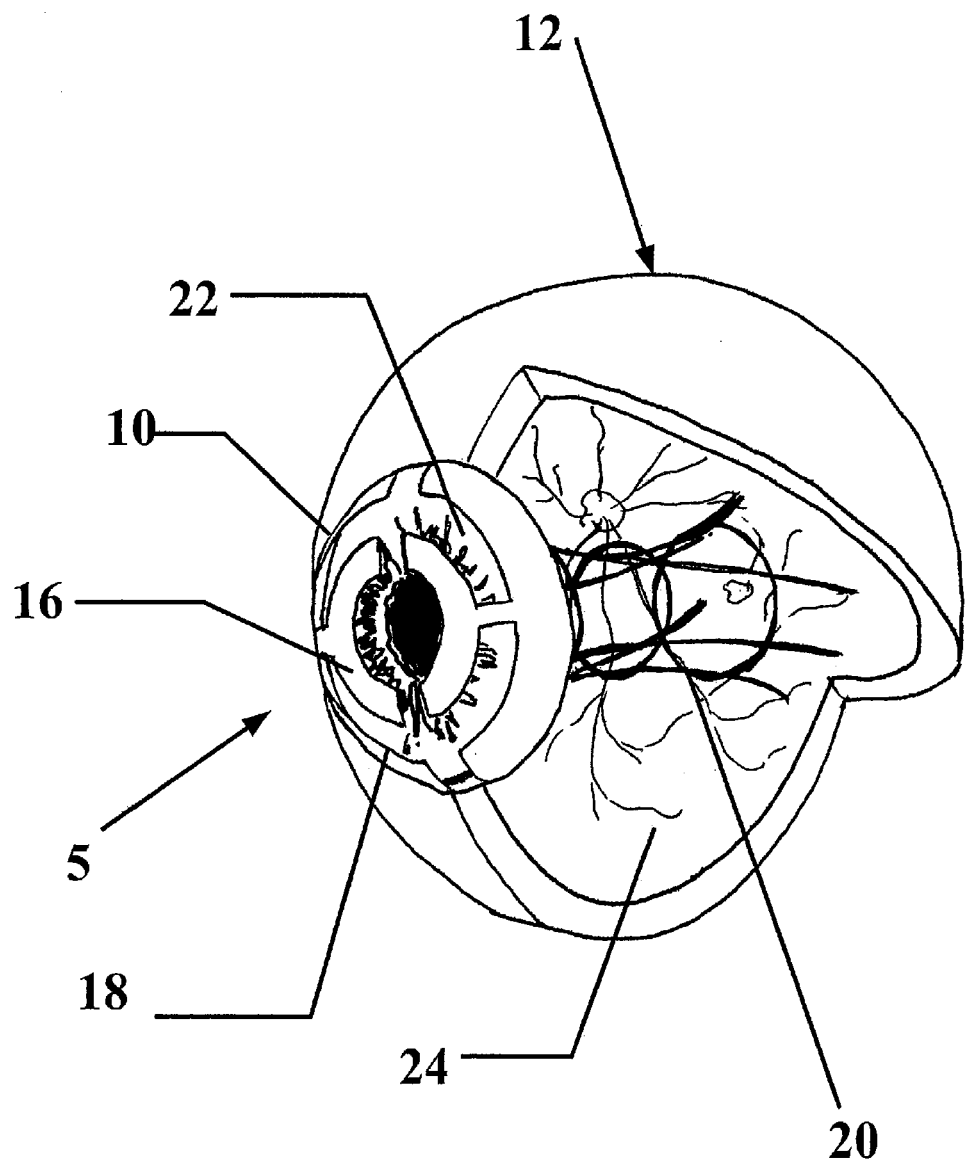
FIG. 4 is a diagram of the Electrical Fields induced by the OSD.

A preferred embodiment of the present invention provides an ocular stimulation device (OSD) 5 having a stimulating contact lens 10 to be worn on the exterior of an eye 12 and makes an electrical contact with the eye 12. Referring to FIG. 1, the contact lens 10 is a clear, flexible, lens; embedded in the lens are stimulating photodiodes 16 and return electrodes 18, which generate an electric field 20 within the eye 12 as shown in FIG. 4. The generation of an electric field 20 provides a therapeutic rescue effect of the remaining visual pathway. The resulting effect is an overall improvement in vision loss and prevents or slows the further progression of Retinal Degeneration or other types of ocular disease.

Figure 2:
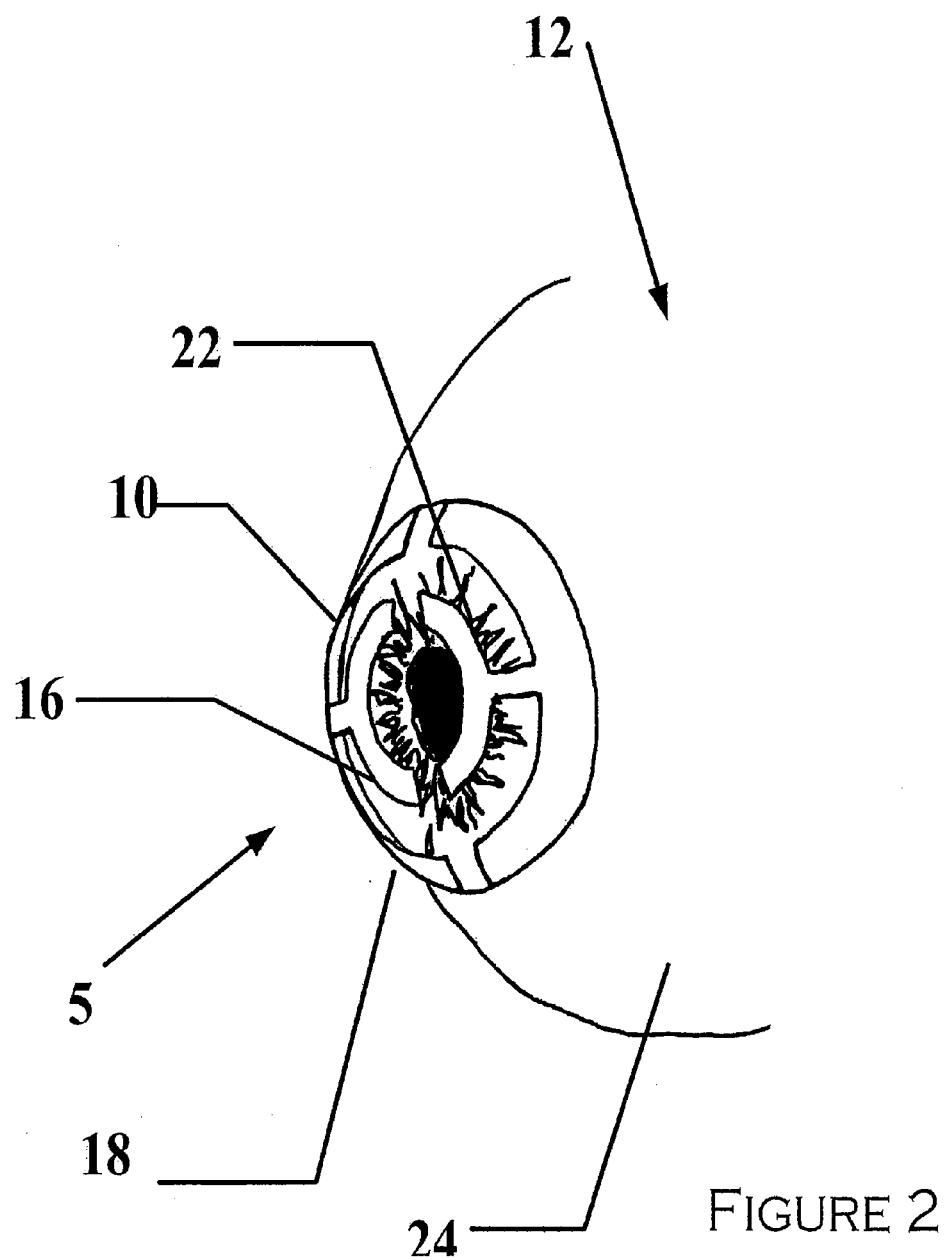
FIG. 2 is a diagram of the OSD applied to the eye, with stimulating photodiodes in contact with the cornea and the return electrodes in contact with the sclera or the eyelid.
Figure 3:
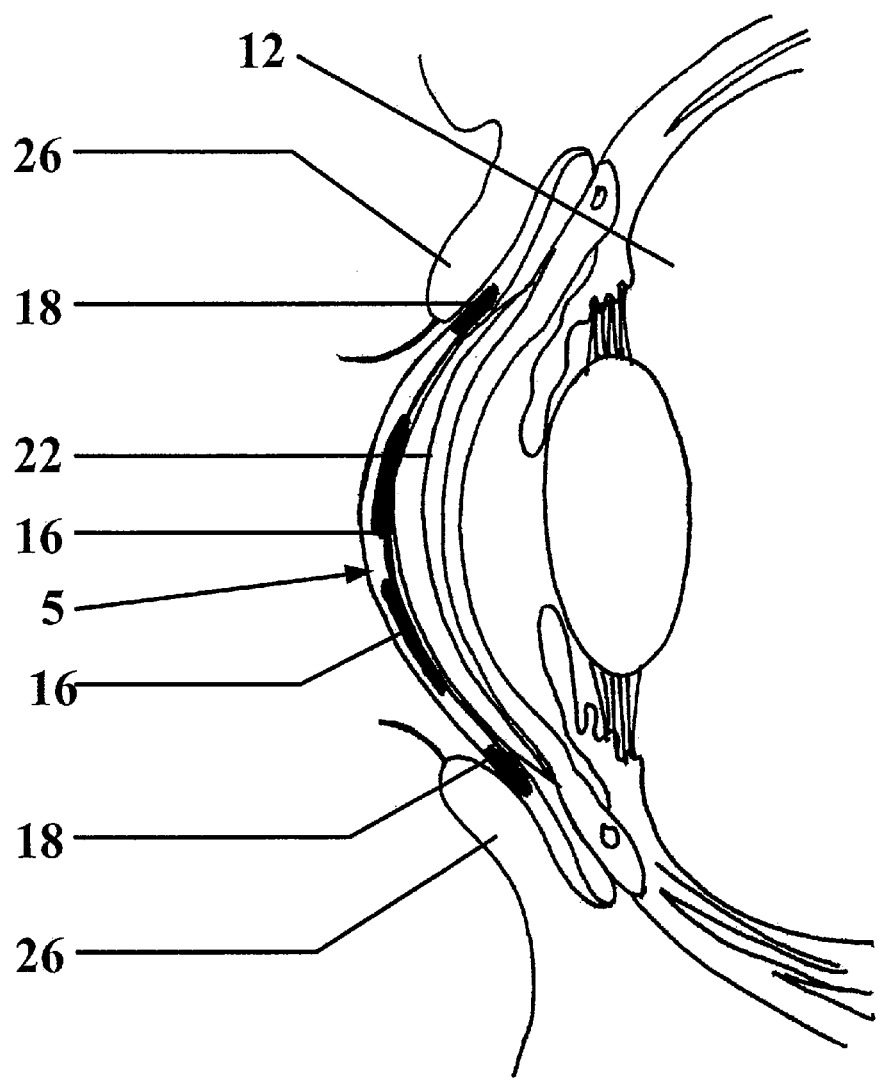
FIG. 3 is a cross-section diagram of the OSD as it sits in contact with the eye. The stimulating photodiodes are in contact with the cornea and the return electrodes contact with the sclera or the eyelid.

The OSD 5, when properly placed on the eye 12 as in FIG. 2, has the stimulating photodiode 16 forming an electrical contact with the cornea 22 of the eye 12. The return electrodes 18 make an electrical contact with either the sclera 24 of the eye 12 or with an eyelid 26 of a wearer (FIG. 3).

Figure 5:
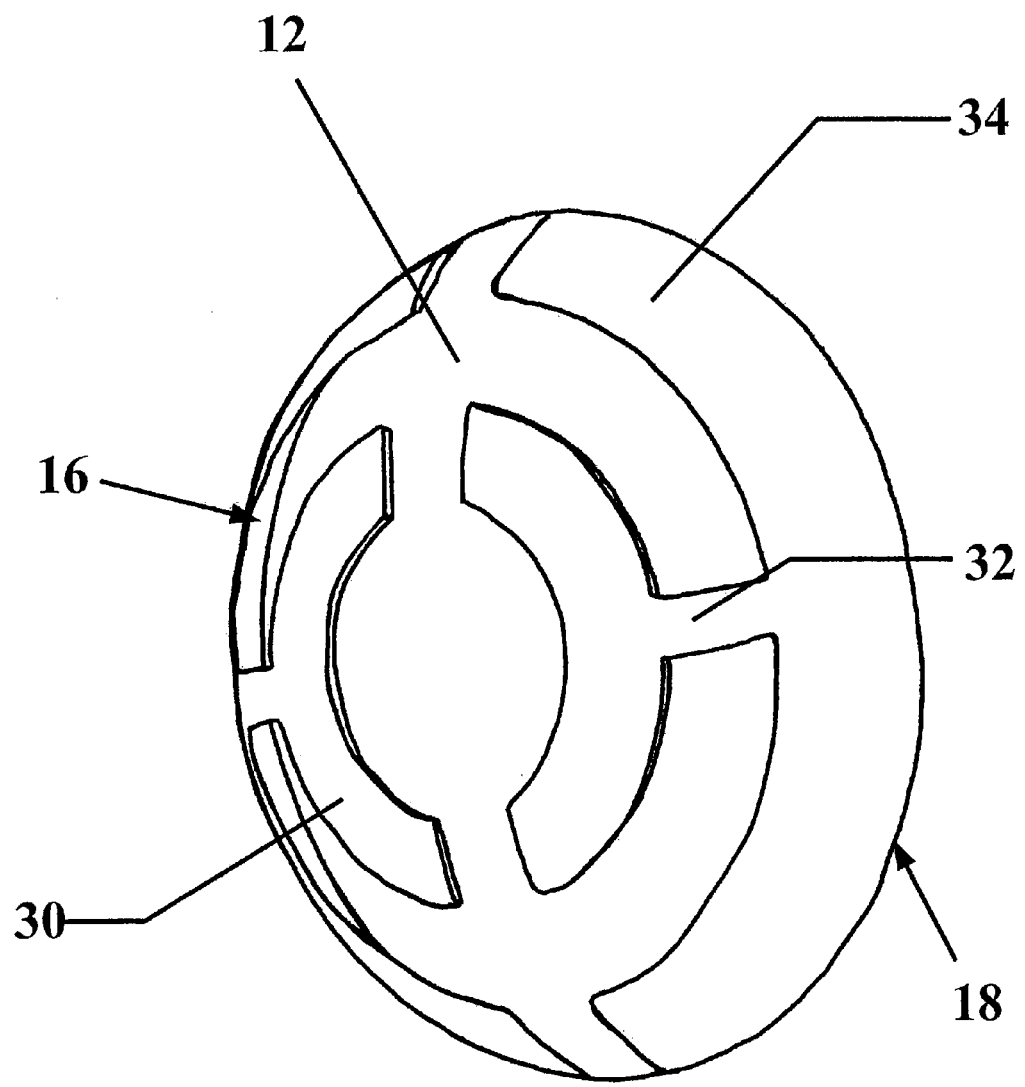
FIG. 5 is a perspective view of the OSD.

The stimulating photodiodes 16 are shown positioned on a central portion of the OSD 5, having two arcuate shaped electrodes 30 dimensioned to border and contact a peripheral portion of the cornea 22. The return electrodes 18 has an axially extending portion 32 connecting to the photodiodes 18 and a circumferentially extending portion 34 for contacting the sclera or eyelid or both as seen in FIG. 5.

Figure 6:
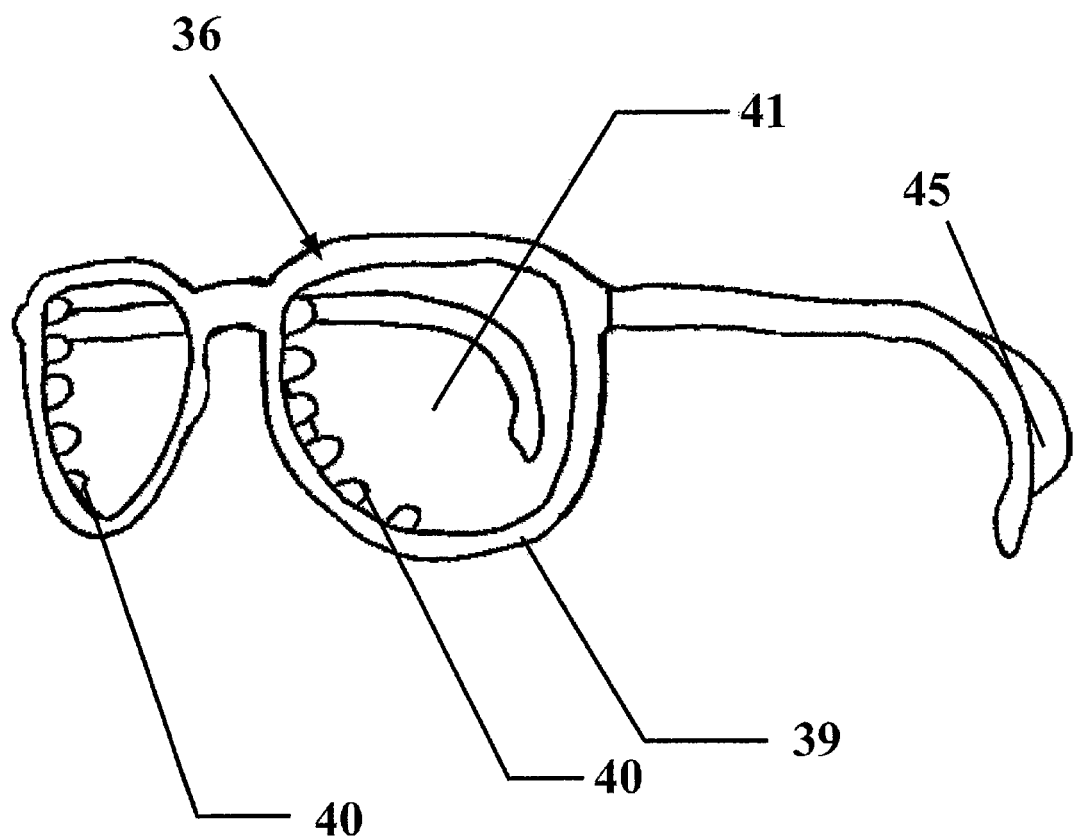
FIG. 6 is a diagram of a pair of stimulating glasses with stimulating LEDs.
Figure 7:
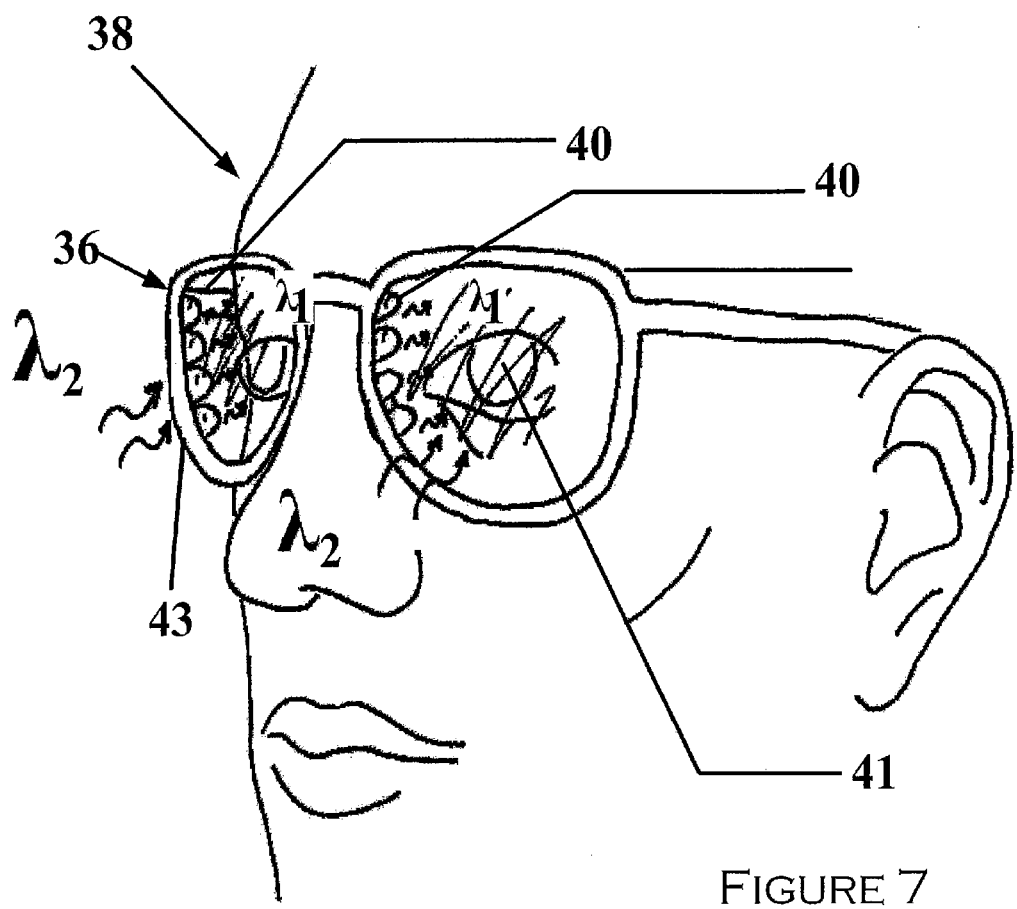
FIG. 7 is a diagram of the stimulating glasses worn by a patient.
Figure 8:
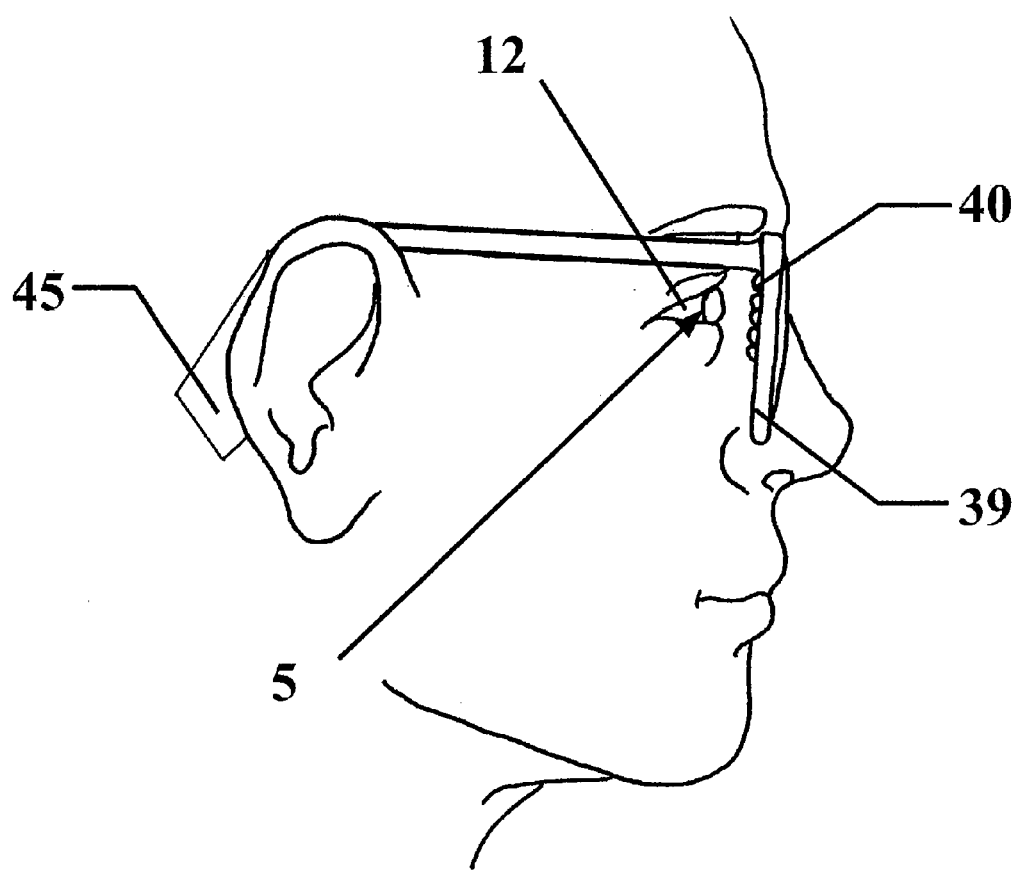
FIG. 8 is a diagram of the OSD worn by a patient also wearing the stimulating glasses.

The OSD 5 provides electrical stimulation to the eye when activated by the electromagnetic radiation or by inductance effect. In a preferred form, a pair of stimulating eye glasses 36 of FIG. 6 provide electromagnetic radiation to the OSD 5. A user or wearer 38, as seen in FIGS. 7 and 8, wears the stimulating glasses 36 which have a frame 39 embedded with light emitting diodes (LED) 40 or another form of light producing elements, and filtered lenses 41. Control circuitry 45 is attached to the frame and preferably in a discrete location as shown in FIG. 8 The LEDs 40 are used in a preferred embodiment and are chosen to provide a certain wavelength of light 43 to which the stimulating photodiodes 16 embedded in the OSD 5 are tuned, and to which the lenses 41 filter.

Specifically, in one embodiment of the invention, the glasses 36 are produced with a low pass lens, a lens that will pass through the entire visible spectrum and reflect the near infrared (NIR) and infrared (IR) wavelengths. In one preferred form, the stimulating photodiodes 16 are chosen to emit a wavelength in the range of 740-1000 nm and more preferably of 880 nm. The stimulating photodiodes 16 on the OSD 5 are tuned to respond to the 880 nm wavelength and produce an electric charge upon incident of that wavelength of light.

Figure 9:
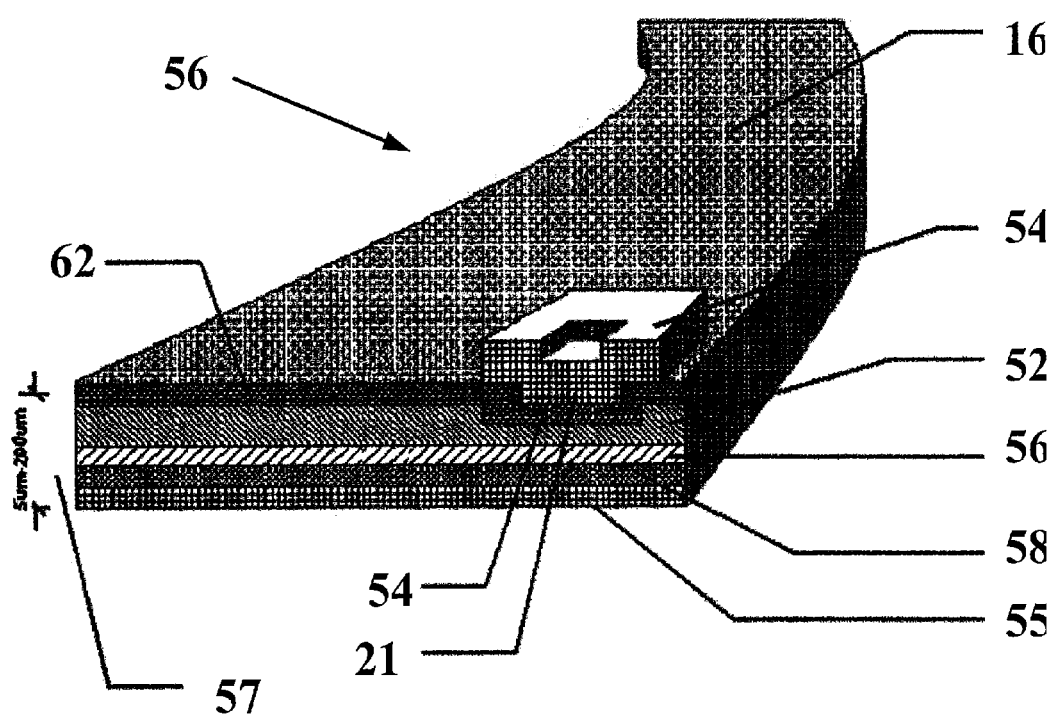
FIG. 9 is a schematic representation of a cross-section of the stimulating photodiodes.

FIG. 9 shows a preferred embodiment of the stimulating photodiode 16 as a PiN photodiode. The PiN electrode can be fabricated from well-known photoelectric materials, such as silicon, selenium, gallium arsenide, etc. The preferred embodiment utilizes a silicon based PiN photodiode.

The stimulating photodiode 16 is manufactured by standard silicon processing techniques. First, a selected N-type wafer 56 is thinned down to the appropriate thickness 57. In a preferred embodiment, the thickness is from about 5 µm to about 200 µm, more preferably from about 20 µm to 100 µm, and most preferably about 29 µm. A layer of silicon oxide is then deposited on the wafer. Metal contacts 54, 55 are provided on opposite sides of the silicon wafer 56. The wafer 56 is then patterned with standard lithography techniques, the silver oxide is etched, and the wafer 56 is doped with an appropriate p-type dopant 52. Additional p+ dopants 54 and n-dopants 58 are applied to the areas of metal contact 54, 55. The wafer 56 is then coated with appropriate thickness of nitrides and oxides to produce an optical filter 62 responsive to the stimulating wavelength of light. The wafer is then patterned for metal coatings and a metal is applied and lifted off to develop the contacts 54 and 55. The wafer 56 is once again patterned for removal from the wafer and the photodiodes are etched out of the wafer. The result after processing is a photodiode with the appropriate thickness, electrical responsitivity to certain wavelengths of light and with the appropriate shape to be embedded into the contact lens.

Figure 10A:
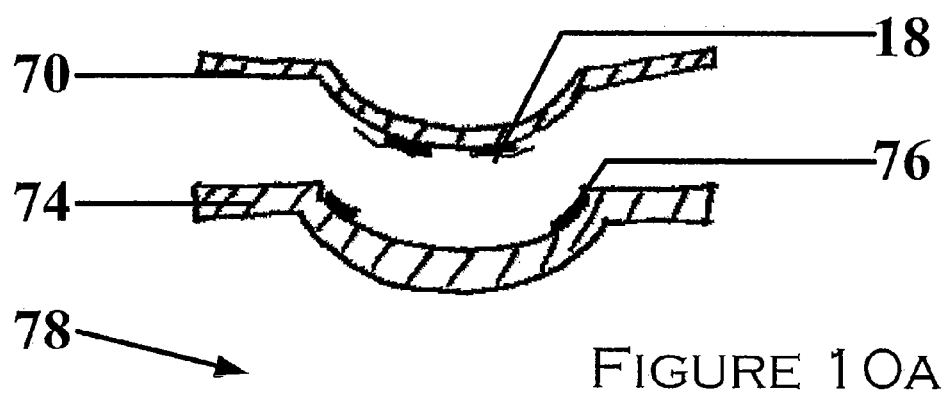
FIGS. 10a-10c show a cross-sectional view of molds used in creating the contact lens OSD and the embedded photonic devices and return electrodes.
Figure 10B:
Figure 10C:
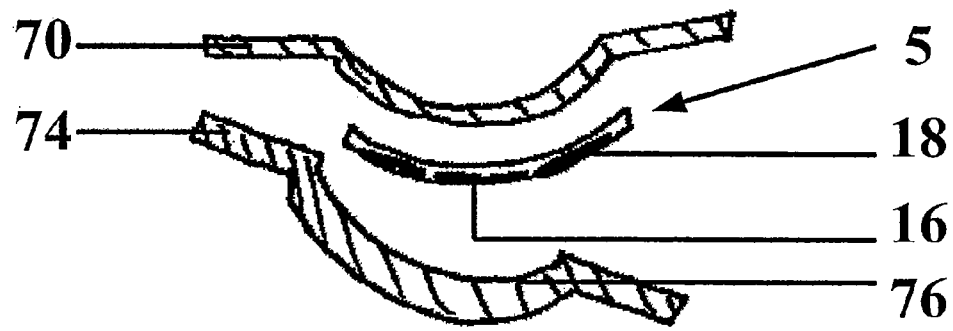

The OSD 5 is manufactured by standard ophthalmic lens techniques using glass or more preferably polymeric materials including substituted and unsubstituted acrylic acid polymers and copolymers and ester and anhydride derivative thereof. Suitable polymers include, but are not limited to, polymethyl methacrylate (PMMA), cellulose acetate butyrate (CAB), polycon, styrene, silicone acrylate, flourosilicone acrylate, carbosifocon, or hydrogel. The contact lens can be fabricated using any technique, such as machining, spin casting or mold casting. A preferred embodiment utilizes a heat cured PMMA process in a cast mold. The PMMA material is inserted into a molding cavity such as that illustrated in FIGS. 10a-10c. When the two mold dies, the concave and convex components are mated together and result in a space relative to the thickness of the lens. The mold can be made to alter the optical properties of the lens and thus also correct for vision.

Figure 11:
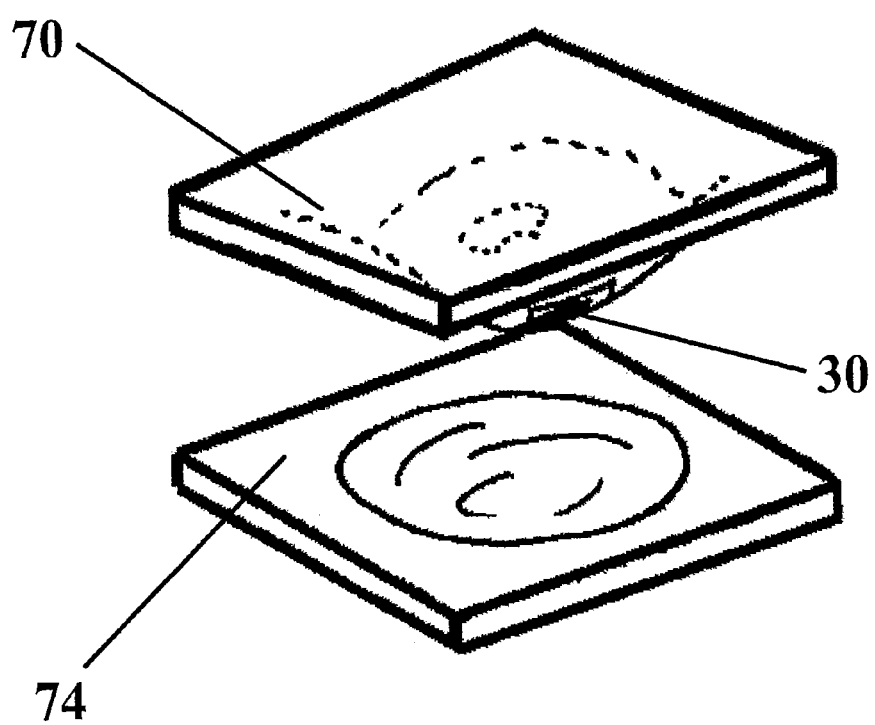
FIG. 11 is an isometric view of the male and female molds used in manufacturing the contact lens OSD.

The convex mold 70 has reliefs 72 etched in it as illustrated in FIG. 11, which correspond to the shape of the manufactured stimulating photodiode. The concave mold 74 is etched with a corresponding relief 76 for the return electrode. The photodiodes are loaded into the convex mold 70 and the return electrode is loaded into the concave mold 74. The PMMA or other material is then placed into the concave mold 74. The convex mold 70 is mated with the concave mold 74. The mated die 78 (FIG. 10b) is then heated to the appropriate temperature allowing for the PMMA to cure. Once cured, the molds are separated and the cured PMMA with semiconductor photodiodes is released. The result is the OSD 5, a contact lens with embedded photodiode stimulation electrodes.

FIG. 12 shows a photodiode for responding to a single wavelength. FIGS. 13 and 14 show a photodiode for responding to two different wavelengths.

Figure 12A:
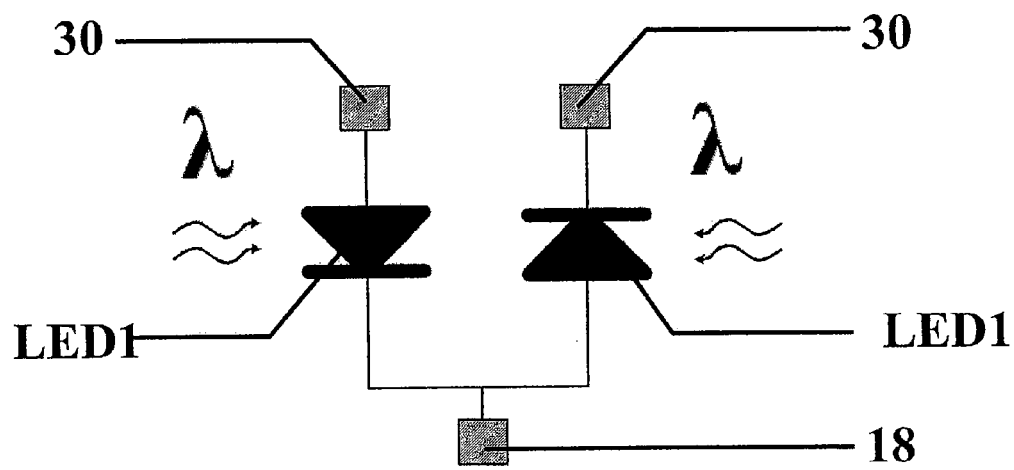
FIGS. 12a and 12b show a schematic of the circuit produced by the OSD in contact with the eye.
Figure 12B:
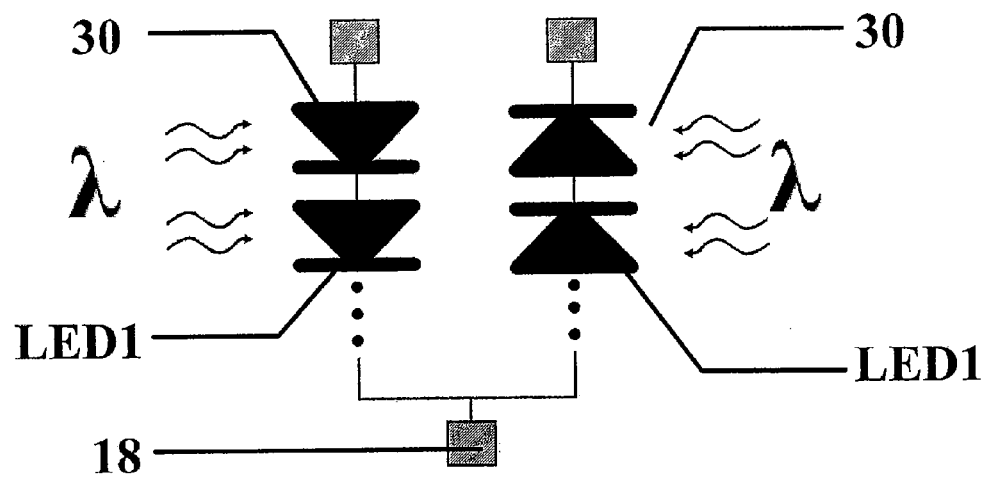
Figure 13A:
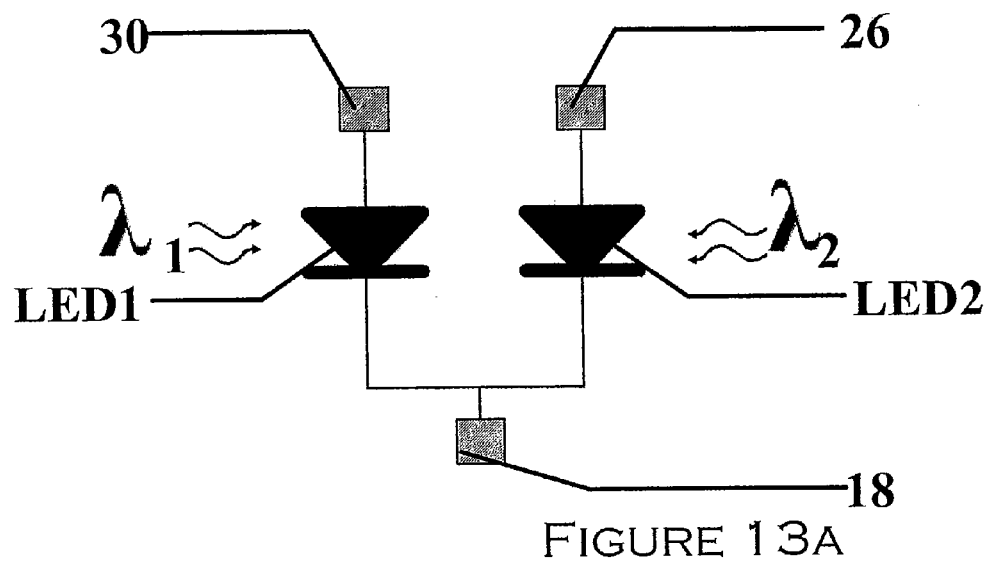
FIGS. 13a and 13b show a schematic of the effective circuit produced by the OSD with different wavelengths of light used.
Figure 13B:
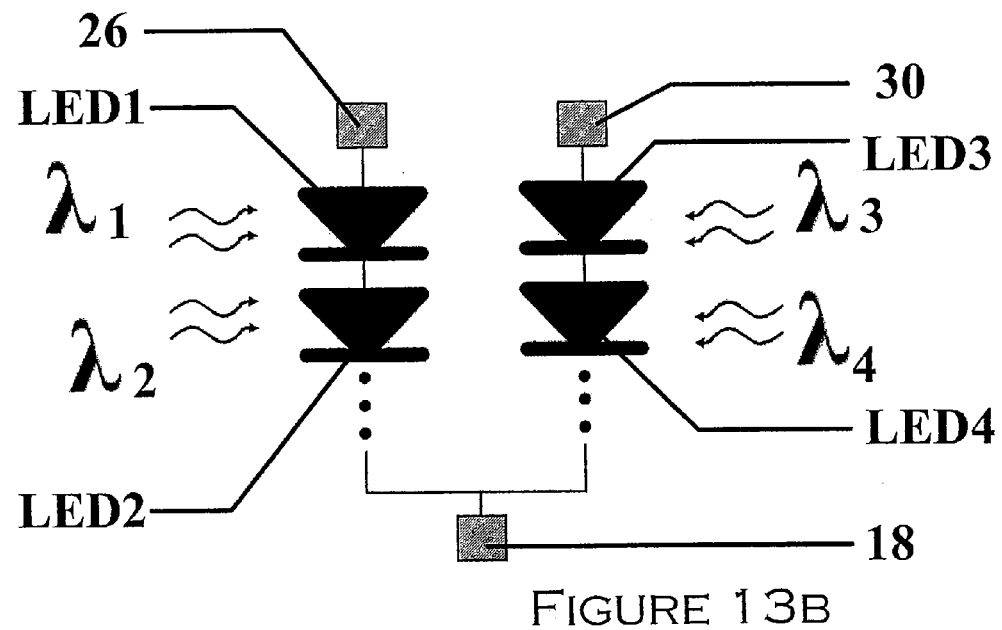
Figure 14A:
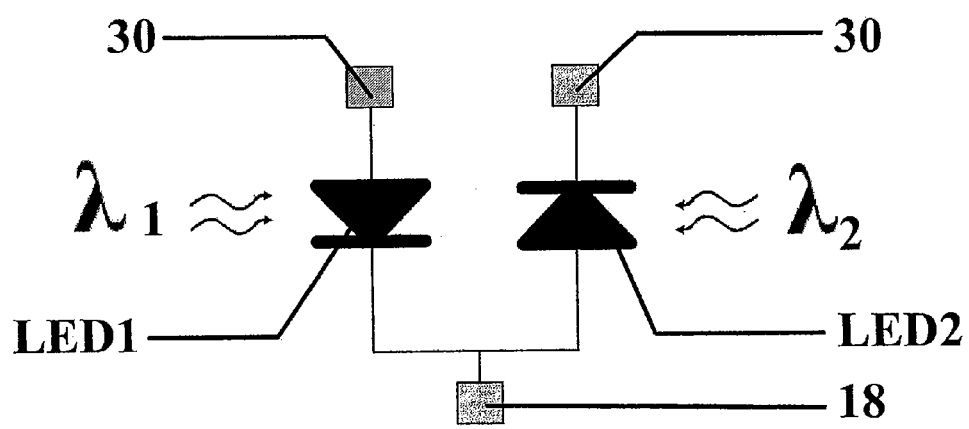
FIGS. 14a and 14b show a schematic of the effective circuit produced by the OSD in a biphasic, anodic/cathodic (A/C) arrangement. Anodic and cathodic stimulation are produced by different wavelengths of light.
Figure 14B:
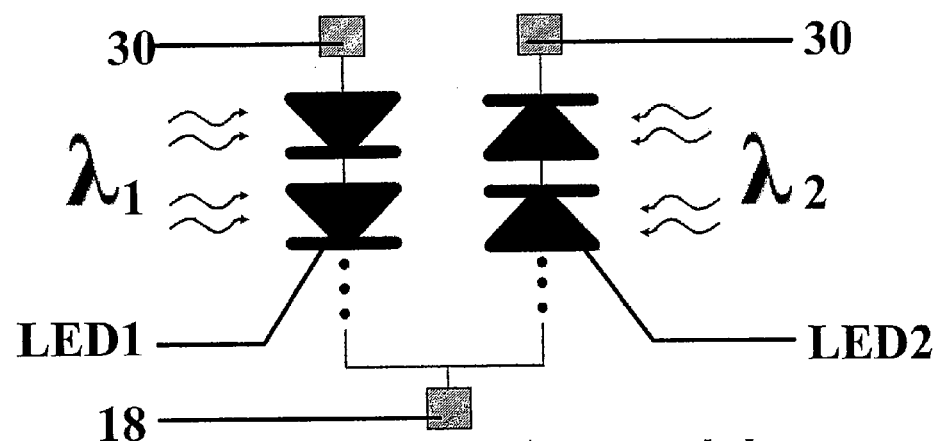

The photodiodes 16 can be arranged in any number of configurations as shown, for example, in FIGS. 12, 13 and 14. Further, the arrangement of photodiodes is not limited to the number of stimulating photodiodes. As few as one stimulating photodiodes can be used and any combination of shunt, parallel (FIGS. 12a, 13a, 14a) or combination of shunt and parallel (FIGS. 12b, 13b, 14b) or other series arrangements can be utilized as well.

Further, the photodiodes can be arranged in such a manner as to provide a biphasic, A/C stimulation by arranging the diodes in an inverse manner as in FIG. 14. In this embodiment, the two photodiodes are tuned to different wavelengths of light and only provide electrical stimulation when excited by that specific wavelength of light.

Figure 16:
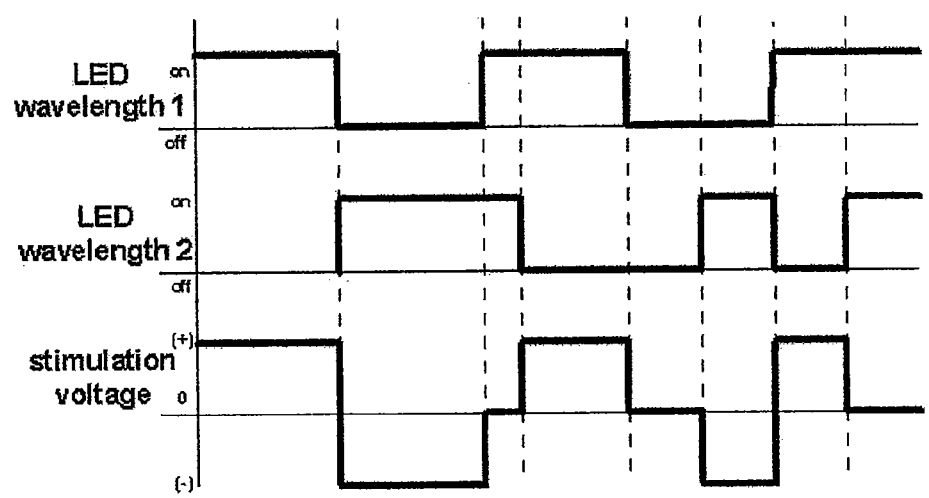
FIG. 16 is a diagram showing the effective input waveforms and resulting stimulation waveforms for a biphasic, A/C device and the resulting anodic and cathodic stimulation waveforms.

In a preferred embodiment, a first photodiode (LED 1) is tuned to 880 nm and a second photodiode (LED 2) is tuned to 940 nm (FIG. 13). When a stimulation light pattern with a wavelength of 940 nm strikes the OSD 5, one side of the OSD 5 will be stimulated and produce a cathodic stimulation. When a stimulation light pattern of 880 nm wavelength strikes the OSD 5, an anodic stimulation occurs. The resulting stimulation is seen in FIG. 16. When LED 1 shines on the OSD 5 with no light from LED 2, then there is a cathodic stimulation. When LED 2 shines on the OSD 5 with no light from LED 1, then there is an anodic stimulation. When there is light from both LED 1 and LED 2, the two stimulation patterns cancel each other, achieving the same stimulation as with no light.

Figure 15:
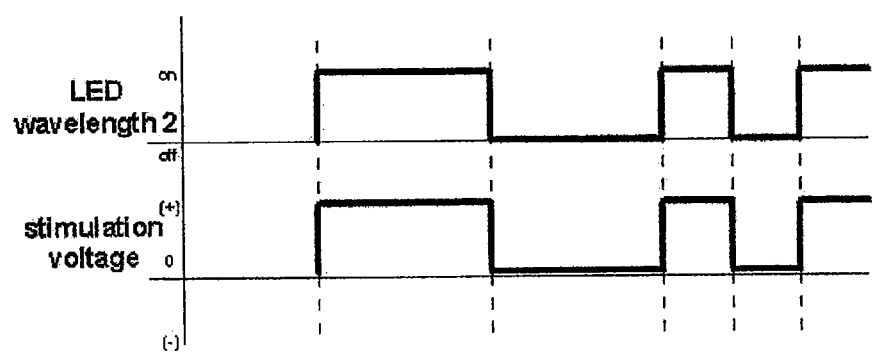
FIG. 15 is a diagram showing the effective input waveforms and resulting stimulation waveforms for a single pole (either anodic or cathodic).

When the OSD 5 is arranged in a manner such as in FIG. 12, then a single wavelength of light 30 will produce the stimulation pattern as in FIG. 15. This same pattern can also be achieved without the use of the stimulation glasses 36.

The present invention further contemplates tuning the stimulating photodiodes to ambient lighting conditions so that the eye glasses 36 and photodiodes 40 are not required in this embodiment.

The effective result of stimulating the eye 12 is an electric field 20 generated in the eye 12. Another embodiment for the OSD 5 is a method for delivering an electric field 20 to release a predisposed drug such as in iontophoresis.

Figure 17:
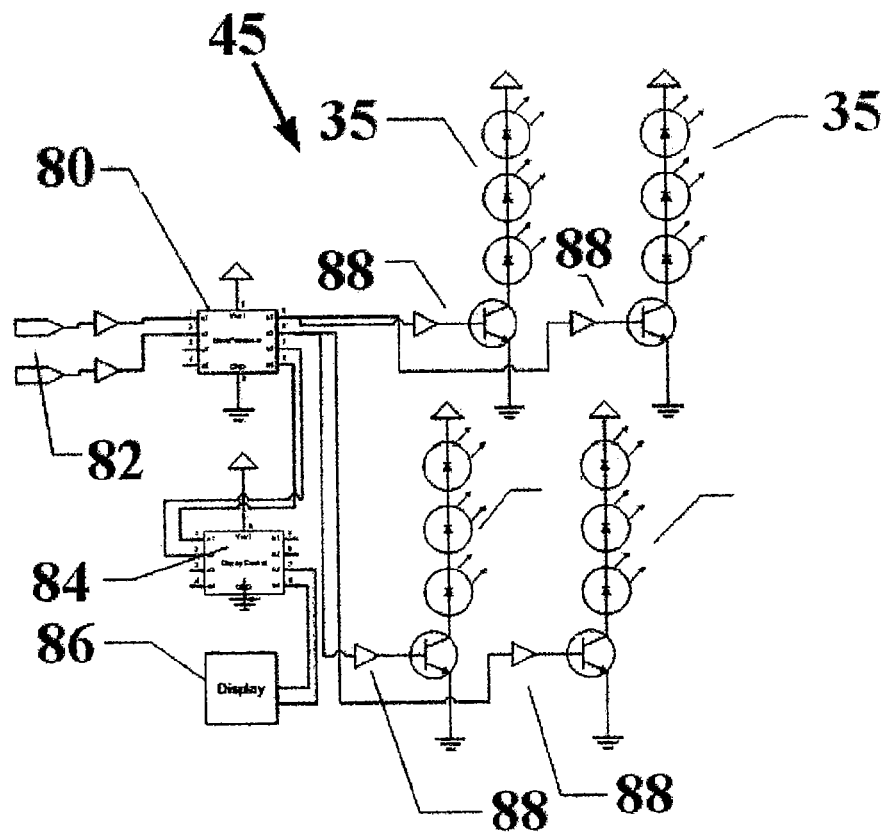
FIG. 17 is a block diagram of the circuitry used in controlling the stimulating LEDs in the stimulating glasses.

FIG. 17 shows the control circuit 45 has a microprocessor 80 with input controls 82, display circuitry 84, a display 86, and switches 88 for activating LED1 and LED2.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention is claimed as follows:

1. An ocular stimulation device, comprising a noninvasive contact lens with a photoconductive member embedded in a surface thereof for electrically stimulating an eye of a wearer of the lens, wherein the member includes a return electrode and a stimulating electrode that is generally centrally disposed on the lens.

2. The device of claim 1, wherein the member comprises a substrate that generates an electrical current to an eye in response to electromagnetic radiation.

3. The device of claim 2, wherein the substrate generates an electrical current to an eye in response to exposure of the substrate to electromagnetic radiation in the near infrared spectrum.

4. The device of claim 3, wherein the substrate generates an electrical current in an eye in response to exposure to electromagnetic radiation in a wavelength from about 880 nm to about 940 nm.

5. The device of claim 2, comprising a plurality of substrates on the lens arranged in series.

6. The device of claim 2, comprising a plurality of substrates on the lens arranged in a combination of a parallel manner and in series.

7. The device of claim 2, wherein the substrate is a photodiode.

8. The device of claim 2, wherein the substrate is a phototransistor.

9. The device of claim 2, wherein the substrate is a solar cell.

10. The device of claim 2, wherein the substrate provides anodic stimulation.

11. The device of claim 1, wherein the substrate provides cathodic stimulation.

12. The device of claim 1, wherein the substrate provides anodic and cathodic stimulation to the ocular system.

13. The device of claim 1, further comprising stimulating eye glasses.

14. The device of claim 13, wherein the stimulating eye glasses have lenses that filter infrared light.

15. The device of claim 13, wherein the stimulating eye glasses have one or more light emitting diodes associated therewith.

16. The device of claim 15, wherein the one or more light emitting diodes emits electromagnetic radiation in the near infrared or infrared wavelengths.

17. The device of claim 16, wherein a first one or more light emitting diodes emits electromagnetic radiation at a first wavelength, and a second one or more light emitting diodes emits electromagnetic radiation at a second wavelength different from the first wavelength.

18. The device of claim 17, wherein the first one or more light emitting diodes emits light at about 880 nm, and the second one or more light emitting diodes emits light at about 940 nm.

19. The device of claim 1, wherein the stimulating electrode comprises two arcuate-shaped electrodes.

* * * * *